(12) United States Patent
Petty

(10) Patent No.: US 6,314,318 B1
(45) Date of Patent: Nov. 6, 2001

(54) DEVICE AND METHOD FOR TREATING INFECTION USING STANDING RADIO FREQUENCY WAVES

(76) Inventor: Norman C. Petty, 5510 Richmond Rd., Mobile, AL (US) 36608

( * ) Notice: Subject to any disclaimer, the term of this patent is extended or adjusted under 35 U.S.C. 154(b) by 0 days.

(21) Appl. No.: 09/708,947

(22) Filed: Nov. 8, 2000

Related U.S. Application Data

(63) Continuation-in-part of application No. 09/489,871, filed on Jan. 20, 2000, now abandoned.

(51) Int. Cl.⁷ .................................................. A61N 1/00
(52) U.S. Cl. ................................................... 607/2
(58) Field of Search ................................. 607/2, 115, 100, 607/101, 116

(56) References Cited

U.S. PATENT DOCUMENTS

| 5,330,481 | 7/1994 | Hood et al. ............................. 606/99 |
| 5,928,217 | 7/1999 | Mikus et al. .......................... 604/530 |

*Primary Examiner*—Scott M. Getzow
(74) *Attorney, Agent, or Firm*—Polster, Lieder, Woodruff & Lucchesi, L.C.

(57) ABSTRACT

An apparatus and process whereby radio frequency (RF) energy is transmitted to a conductor, creating a standing wave on this conductor. This standing wave travels along the surface of the conductor through the skin effect, and this standing wave kills microorganisms, including prokaryotic cells (bacteria), that are lying along the surface of the conductor.

10 Claims, 4 Drawing Sheets

DEVICE AND METHOD FOR TREATING INFECTION USING STANDING RADIO FREQUENCY WAVES

CROSS REFERENCE TO RELATED APPLICATIONS

This is a continuation-in-part of application Ser. No. 09/489,871, filed Jan. 20, 2000, now abandoned.

STATEMENT REGARDING FEDERALLY SPONSORED RESEARCH OR DEVELOPMENT

Not Applicable

BACKGROUND OF THE INVENTION

1. Field of the Invention

This invention relates to the field of electrotherapeutic methods, and more particularly to methods of treating infections through the use of electromagnetic waves.

2. Description of Related Art

When a person injures a bone so that an orthopedic surgeon is required to incise the person and place a mechanical device to stabilize the bone, most often the device that is placed is a metal alloy. This "implant" is used to strengthen the bone and hold it mechanically stable while the cells of the bone grow over the defect ("knit"). In some instances, the bone and "implant" will become infected.

Currently, the standard procedures for an infected implant are either re-incision of the patient and removal of the implant, or infusion of an antibiotic for a protracted period of time, with subsequent re-incision and removal of the implant if the infection persists. The first solution requires that the patient be taken to an operating suite, anesthesized with a general anesthetic, and then connected to monitors and support devices, such as an endotracheal tube placed to control his breathing, IV lines to administer fluids and blood, urinary catheters, etc. The new, sterile implant is placed immediately, exposing the affected area as filly as during the first operation and then physically removing the infected implant, irrigating the infected area, and then placing a new sterile implant.

In other situations, the surgeon may allow the patient to heal six weeks without the implant, and then re-incise the patient and re-introduce another implant During this six week period, the patient is usually treated with intravenous (V) antibiotics to try to kill the bacteria causing the infection.

In another method, a surgeon will elect to begin with a six week regimen of IV antibiotics, and if the medication does not work satisfactorily, or if the patient's condition deteriorates, then the surgeon will elect to remove the infected implant and replace it, as discussed above. Specific problems encountered during the above procedures include an increased risk of mortality (death) and morbidity (inability to function normally) for every instance that an individual has to undergo a major surgery in which he is placed under general anesthetic.

Furthermore, there is a significant cost borne by the patient in having a second major surgery. The cost includes the operating suite, surgeons time, the stand-by surgeon's time, the cost of a second implant, and the cost of the hospital stay after the operation to recuperate sufficiently to be discharged home.

Improvements to removal of the implant have been suggested. For example, U.S. Pat. No. 5,330,481, issued on Jul. 19, 1994 to Hood et al., teaches a method of using ultrasonic energy in the range of 20,000 to 40,000 Hertz (20 KHz–40 KHz) at from between 50 and 800 watts power for implantation or removal of an osteal prosthesis. However, that reference does not teach the sterilization of an implant without removing the implant from a human subject.

Methods of killing eukariotic cells, such as benign or malignant cancer cells, through sufficient heating with radio frequency (RF) energy have been proposed. For example, U.S. Pat. No. 5,928,217, issued on Jul. 27, 1999 to Mikus et al. discloses the use of a stent system for treatment of prostate tumors in which RF energy in an undisclosed frequency at from between 20 to 40 watts to raise the temperature of the stent to at least 40° C. (104° F.), and preferably 60° C. (140° F.) for between 10 and 40 minutes to destroy the eukariotic tumor cells. However, that reference does not disclose a method of killing prokaryotic cells through a standing wave of RF energy without decernable heating.

BRIEF SUMMARY OF THE INVENTION

The present invention involves a novel process whereby radio frequency energy (RF) is transmitted to a conductor, creating a standing wave on this conductor. This standing wave travels along the surface of the conductor through the skin effect, and this standing wave kills microorganisms, including prokaryotic cells (bacteria), that are lying along the surface of the conductor. It is believed that the prokaryotic cells are killed by either lysing their external membrane or disrupting their DNA to an extent that they can no longer survive. This invention uses Gigahertz frequency RF in the range of eight to twelve point four GigaHertz (8–12.4 GHz), with a minimum power level of 100 milliwatts required to get microorganism destruction. There has been no recorded conductor surface temperature rise, even when the RF has been applied to the conductor for 160 seconds. Using a thermometer that is accurate to 0.1 degree C., no detectable temperature variance was found between the conductor before and immediately after the RF energy in the foregoing range was imparted to the conductor.

BRIEF DESCRIPTION OF THE SEVERAL VIEWS OF THE DRAWINGS

The objects of the invention are achieved as set forth in the illustrative embodiments shown in the drawings which form a part of the specification.

Corresponding reference characters indicate corresponding parts throughout the several views of the drawings.

DETAILED DESCRIPTION OF INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the constructions described herein without departing from the scope of the invention, it is intended that all matter contained in the description or shown in the accompanying drawings shall be interpreted as illustrative and not in a limiting sense.

Figure 1:
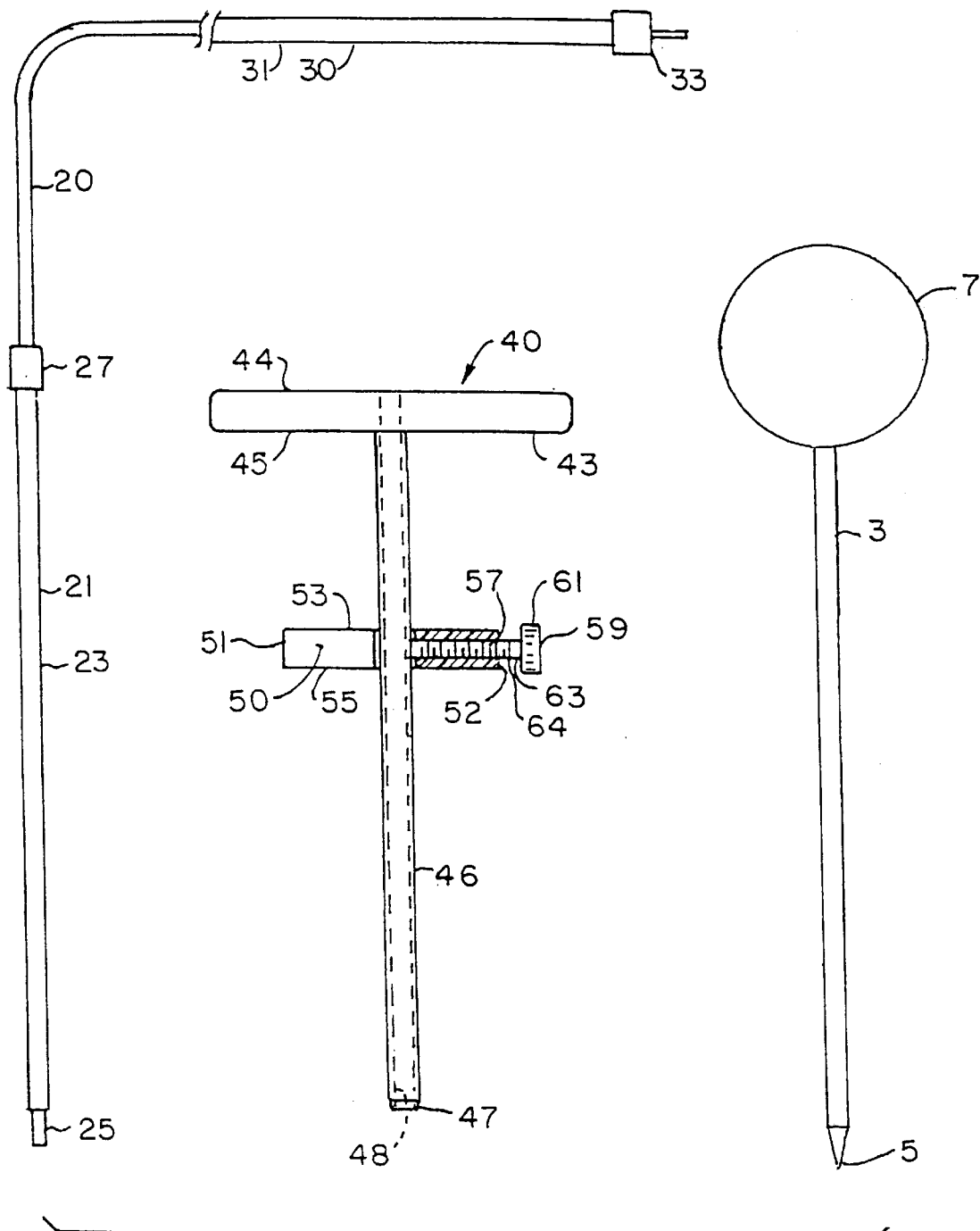
FIG. 1 is a view in side elevation of the components of a delivery needle assembly of the present invention.

Referring now to FIG. 1, a delivery needle of the present invention has three primary components: a needle 3, a transmission needle 20 and a guide assembly 40.

Needle 3 is preferably a trochar needle or stylet having three longitudinally disposed faces, a triangular point 5 and a head 7. Each face of the trochar needle is preferably about one-eighth of an inch in width (about 1.9 mm), and the length will vary depending upon the depth of the implanted conductor to be treated, with a three inch (about 75 mm) length being generally appropriate.

A transmission needle 20 of the present invention is preferably an insulated twelve gauge copper wire, and the needle 20 has an insulated portion 21, an exposed portion 25 at one proximal end 23, and an RG-223 μRF cable 30 with an SMA male connector 33 at its other, distal end 31. The proximal end 23 and distal end 31 are joined in any convenient way, with a soldered connection being preferred. An adhesive depth control 27 may be attached to assist in placement of the transmission needle 20.

The guide 40 has a handle 43 having a top surface 44 and a bottom surface 45. A shaft portion 46 has a beveled end 47 and a longitudinal bore 48 therethrough. A cross-piece 50 is spaced from the handle 43 on shaft 46. The cross-piece 50 has a left side 51 and a right side 52, an upper surface 53 and a lower surface 55. The right side 52 of cross-piece 50 has an internally threaded bore therethough, which is generally transverse to the shaft bore 48 and intersects said shaft 46. A set screw 59 has a head 61 and a threaded shank 63. The treads 64 cooperate with those of the internally threaded bore 48.

Figure 2:
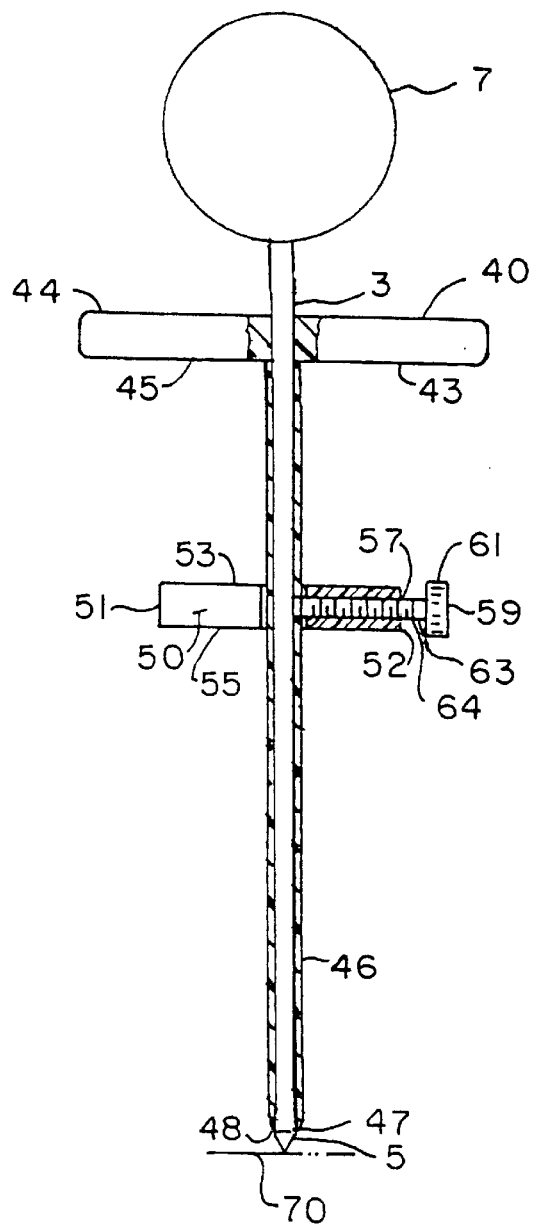
FIG. 2 is a view in side elevation, partly in section, of an assembled guide and trochar needle of the present invention.

Referring now to FIG. 2, the trochar needle 3 is inserted into the guide 40 through the centrally disposed bore 48 of the shaft 46 until the point 5 of the trochar needle 3 is exposed through beveled end 47. When the desired depth of trochar needle 3 is achieved, i.e. the conductor 70 is reached, the trochar needle 3 is withdrawn from the guide 40. The set screw 59 is engaged to the guide 40 to prevent closure of the wound when the trochar needle 3 is withdrawn. In this preferred embodiment, the conductor 70 is a metalic prosthesis.

Figure 3:
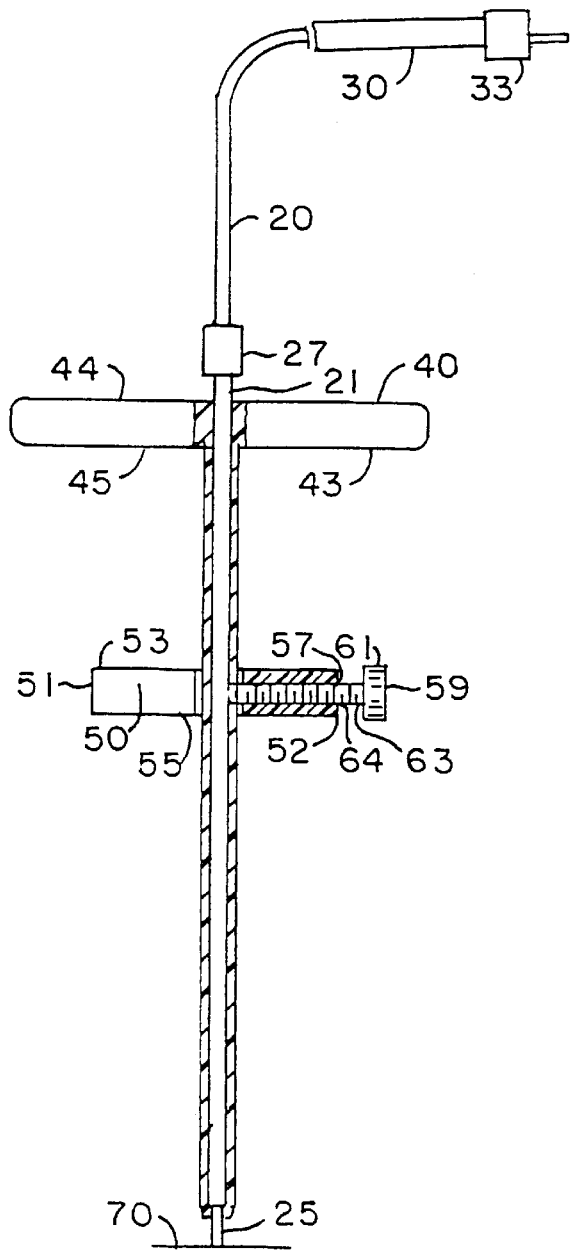
FIG. 3 is a view in side elevation, partly in section, of an assembled guide and transmission needle of the present invention.

Referring now to FIG. 3, after the trochar needle 3 is removed from guide 40, the transmission needle 20 is inserted through bore 48 of shaft 46 until it comes into contact with the conductor 70.

Figure 4:
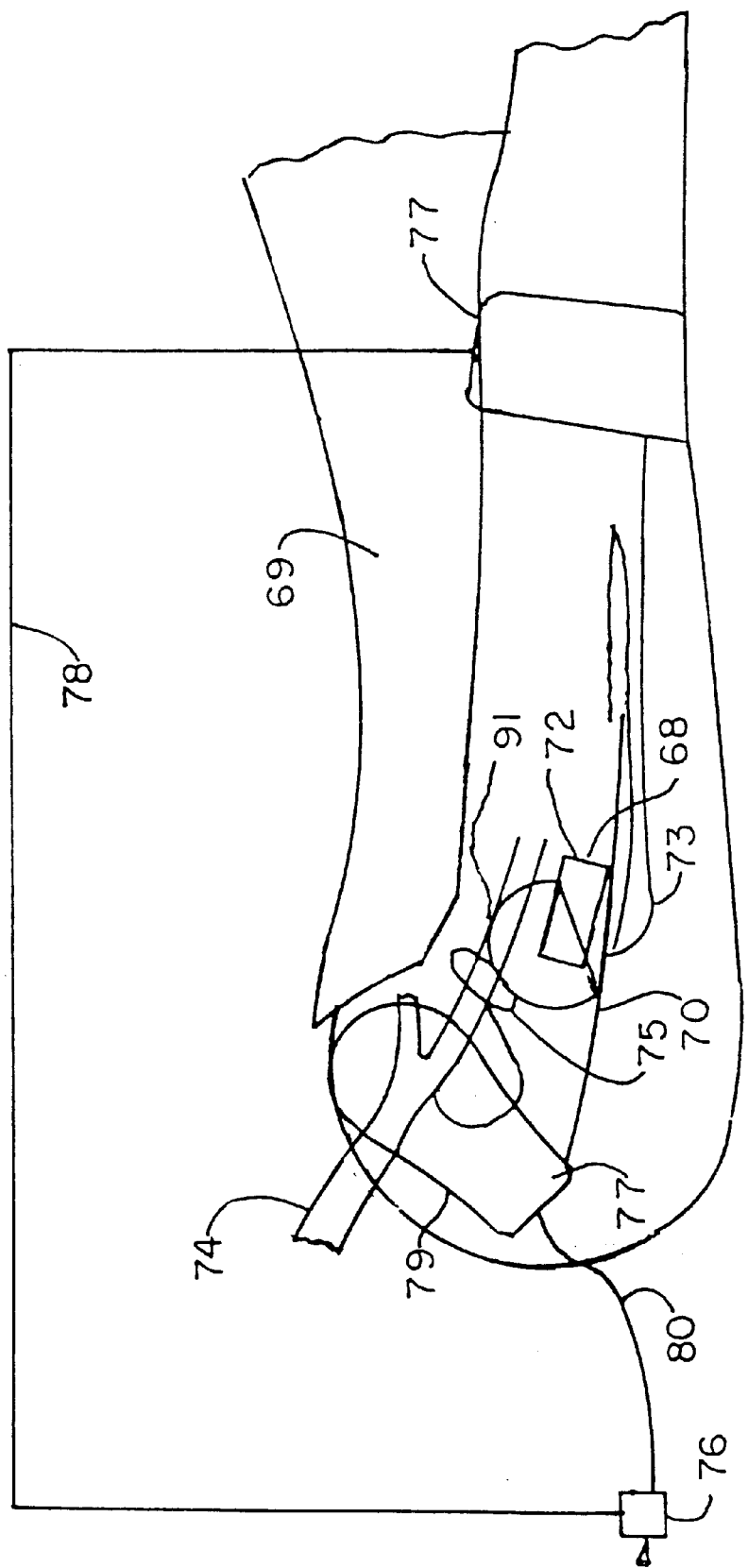
FIG. 4 is a cross sectional detail view of an exemplary placement at a treatment area of the present invention.

FIG. 4 shows a detail view of an exemplary placement of the transmission needle assembly. Referring to FIG. 4, an anatomically safe region 68 on a patient is selected by the user, and a sterile drape 69 is placed over the surrounding m&e The anatomically safe region 68 is determined based upon the type and location of the prosthesis used, and the preference of the treating physician. An implanted conductor 70 is within the anatomically safe region 68. The anatomically safe region 68 in this example is a region lateral to the pubic bone and lateral to the femoral vessels 75 on the femur between the lesser trochanter 72 and the greater trochanter 73, well away from the femoral vessels 75 which branch from the aorta 74.

A toggle switch 76 is provided for selection of a first electrode ground 77 through a first conductor wire 78, or a second electrode ground 79 through a second conductor wire 80.

Figure 5:
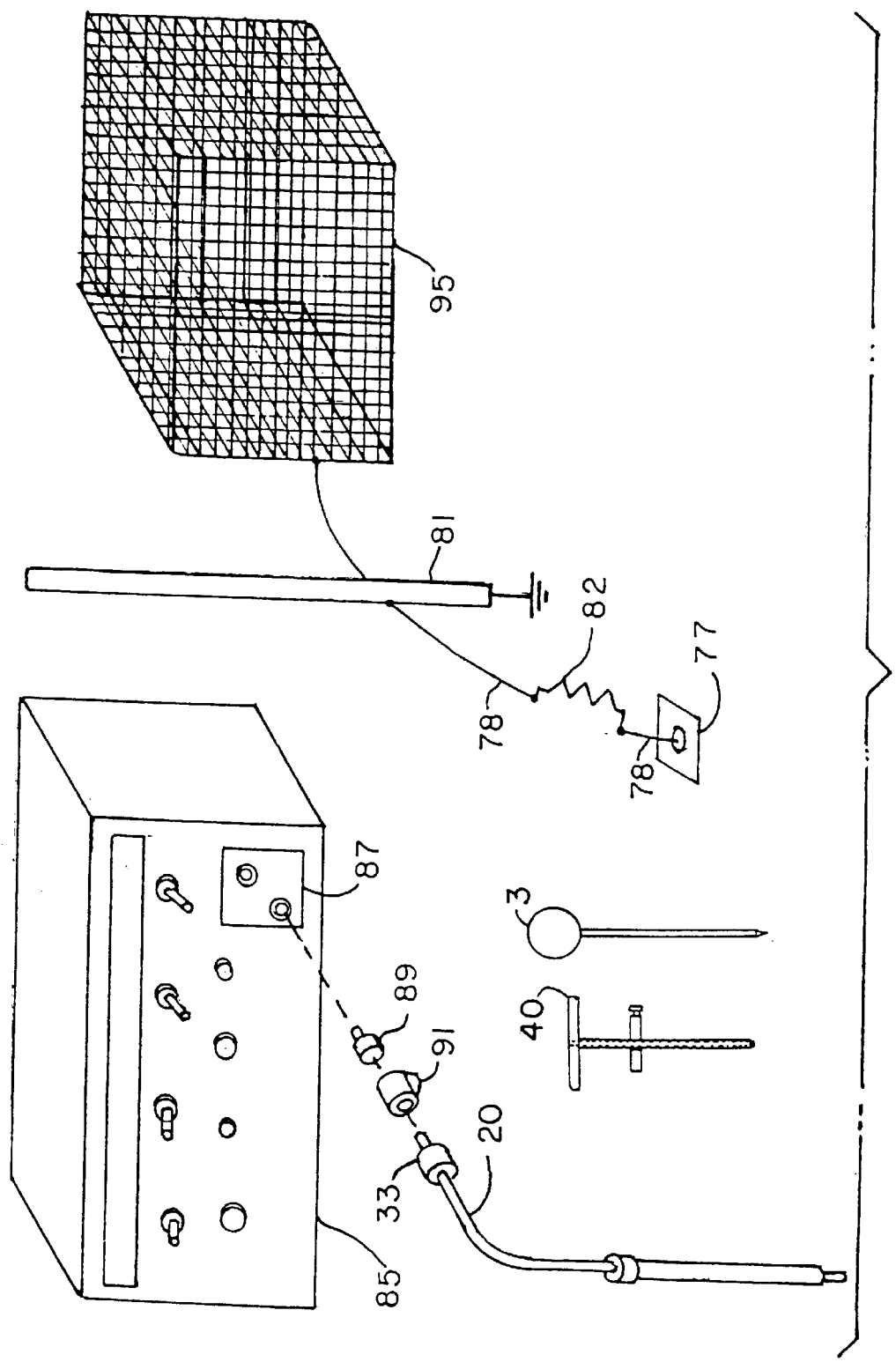
FIG. 5 is a perspective view of a transmission and dispersion assembly of the present invention.

Referring now to FIG. 5, an oscillator 85 is provided for generation of radio frequency energy. In the preferred embodiment of the present invention, the oscillator 85 is a Hewlett Packard Sweep Oscillator model 8690B. An associated plug-in module 87 provides radio frequency waves in the desired wave length. In the preferred embodiment of the present invention, a wave length of between seven and twelve and one half gigahertz (7–12.5 GHz) has been found to be effective. Therefore, a preferred plug-in module 87 is a Hewlitt Packard 8694B plug-in module that generates frequencies in the range of 8.0 to 12.4 GHz. Ths particular module has an N type female connector for output of radio waves, so for the present invention, an SMA male to N male adapter 89 is fitted to module 87. A KU band isolator 91 removes spurious radio wave frequencies. Finally, the transmission needle 20 is attached to isolator 91 through SMA male connector 33.

The electrode ground 77 is attached to the first wire 78. In the preferred embodiment of the present invention, a dual dispersive electrode, available from CONMED Corporation under the trademark THERMOGARD, reference number 51-7310 is used. The grounding wire 78 is parted about twelve inches distant from the electrode 77, and a resistor 82 is soldered between the parted ends of grounding wire 78. In this preferred embodiment, a 47Ω, ½ watt, 5% tolerance resistor, available from RADIO SHACK® as part number 271-1105 is used.

The RF is then delivered to a conducting orthopedic prosthesis 70 that has a microorganism culture in intimate contact with it. The RF is "drawn" along the conductor 70 to the ground 81 by impedance-matching the input impedance to the ground impedance. In the preferred embodiment, the electrode 77 is folded in half around the conductor 70, and then secured with two pairs of forceps to ensure appropriate ground contact. (not shown) The remainder of the grounding wire 78 from the electrode 77 is soldered to the distal end of the resistor 82, and then soldered to the ground 81. The ground wire 78 is then connected to an appropriate grounding point. The ground wire 78 is then secured to a Faraday cage 95, to which the electrode grounding wire is finally attached.

The present invention is preferably calibrated prior to use. Calibration of the power output of the present invention is accomplished through a detector designed to use a digital multi meter, such as a digital multimeter available from WAL-MART as model DM-301 (not shown). Removing the RF cable from the KU band isolator, the detector has an SMA-male connector attached to RG 223 cable proximally. Distally there is an F-type female connector, attached to the F-type male connector on the proximal end of a 1 GHz video detector (not shown). The distal end of the video detector has another F-type male connector, which is attached to an F-type female connector that is on the proximal end of RG-58 C/U cable, which is 18" long (not shown). The distal end of this cable is stripped for 2", and the shielding is soldered into one "banana plug" (ground), while the center pin is soldered into another banana plug (hot). These banana plugs are attached to the multimeter in the hot and ground connections. Operation of this detector, with the multimeter in the 2000 m (2,000 millivolts) setting, allows the power level to be detected and displayed on the multimeter (since there is a direct correlation between the power level and the voltage, P=IE where P=power, I=current, and E=voltage, reading the output voltage provides the ability to find the output power peaks of the sweep oscillator.

EXAMPLE 1

An exemplary method of using the present invention was tested, with excellent bactericidal results. A Hewlett Packard model 8690B sweep oscillator was selected as the source of RF energy, with a Hewlett Packard model 8694B plug in module to produce the required frequency. An N-male to SMA-male connector was attached to the RF output. A KU-band isolator was attached to the SMA-side of the connector, making sure that the "I" designation of the isolator was the transmitted (proximal) and not the reflected (distal) side.

The front panel controls of the sweep oscillator were adjusted as follows: Initially, the "Power" knob was turned to "0". The "ΔF" (delta-f) button on the left bank of buttons was depressed. The "Sweep Selector" knob was turned to "CW". The far left knob, designated as "start/CW" was turned to the desired frequency of 12.125 GHz.

The sweep oscillator was activated by switching the "Line" toggle switch in the bottom left corner of the front panel to the "ON" position. The toggle switch is a 3-position toggle switch; in the far left position the equipment is off, in the middle position, the 'on' position, the equipment is on but it is not transmitting; in the far right position, the sweep oscillator is on and transmitting. This sweep oscillator required at least 5 minutes to warm up before transmitting.

Next, a detector was attached, as described above, to the isolator to check the output power level. The multimeter was switched on, with the selector in the "2000 m" position. With the transmission needle properly shielded, the "Line" toggle switch was turned to the far right (transmit) position. The power level was increased to "10". The "Start/CW" knob was turned until the multimeter display showed a numeric peak (above 1200). Next the power was turned down to "0", the detector was disconnected from the isolator and then connection from to the cable/Delivery needle to the isolator was established, as described above.

The conductor was cultured with a strain of Staphylococcus (S. epidermidis) until a slime layer developed, simulating an acute infection. Sterilization of the conductor was achieved by attaching a grounding electrode distally to the conductor. Application of the transmission needle on the conductor a distance from the ground electrode was next established. When assured of proper contact between the transmission needle and the conductor, the power control knob was turned to "10" for a maximum of five seconds. Temperatures were found to remain constant throughout the treatment, and using a thermometer accurate to within 0.1° C., operatively attached to the conductor, no heat increase was found. A logarithmic death of the culture used was observed, with the slime layer being disrupted and the bacteria therein apparently killed.

EXAMPLE 2

In vivo operation of the present invention may be accomplished as follows. The N-male to SMA-male is operatively connected to the connector to the RF output Next the KU-band isolator is attached to the SMA-side of the connector, making sure that the "I" designation of the isolator is the transmitted (proximal) and not the reflected (distal) side.

The front panel controls of the sweep oscillator are adjusted by first turning the "Power" knob to "0. The "ΔF" (delta-f) button on the left bank of buttons is then depressed. The "Sweep Selector" knob is set to "CW". Then using the "start/CW" knob, set the frequency to about 12.125 GHz.

The sweep oscillator is turned on by switching the "Line" toggle switch on the sweep oscillator to the "ON" position. The sweep oscillator requires at least 5 minutes to warm up before transmitting.

The output power level is checked by first attaching the detector, described above, to the isolator. The multimeter is then turned on, with the selector in the "2000 m" position. With the transmission needle properly shielded, the "Line" toggle switch on the sweep oscillator is turned to the transmit position. The power level is next turned up to "10". The "Start/CW" knob of the sweep oscillator is adjusted until the multimeter display shows a numeric peak, above 1200. The power control of the sweep oscillator is then turned down to "0". The detector is then disconnected from the isolator. The cable/Delivery needle is then connected to the isolator.

To sterilize the conductor: The "anatomically safe" region where the physician has determined to insert the delivery needle is anesthetized. Using sterile technique, the area is prepared and draped. Anesthetization is accomplished by using a three inch 18 to 21 gauge needle to deliver local anesthetic to the anatomically safe region in increments of approximately 1 centimeter per dosage. This requires inserting the needle, applying a wheal of anesthetic, then advancing the needle, applying another dosage, and continuing until the conductor has been contacted, delivering a final dosage at the level of the conductor. The anesthetic needle is then removed.

With the delivery needle attached to the isolator, the guide and trochar needle is advanced to the proper depth, within the anatonically safe regions through the same puncture site made by the anesthetic needle, until the trochar needle contacts the conductor. The depth control is then slid down to the skin level and the knurled knob is tightened so the depth control will not move. The trochar needle is removed and the transmission needle is inserted to the same depth. When proper contact between the transmission needle and the conductor is assured, the power control knob of the sweep oscillator is turned to a level of "10" for a maximum of five seconds. When the approach to the conductor does not allow pure proximal contact with the conductor, a second grounding electrode may be placed proximally, with the two grounding electrodes attached to a two-position toggle switch, to allow either one to be selected. (See FIG. 4). When two grounding electrodes are used, the toggle switch is positioned from the first position to the second position The power control knob of the sweep oscillator is turned to level "10" for five more seconds. The power control knob of the sweep oscillator is then turned to "0". The transmission needle is removed, pressure is applied to the puncture site until bleeding stops, and a sterile dressing is applied.

Numerous variations will occur to those skilled in the art in light of the foregoing disclosure. For example, the trocar needle could be replaced by any implement effective to reach the implanted conductor. Although a frequency of from between 7.0 GHz to 12.4 GHz is utilized, it is believed that higher frequencies could be employed in the production of a standing wave on the conductor, up to 15 TeraHertz (15 THz). Although the exemplary method is described as being suitable for implanted conductors, other conductors could be sterilized, such as the hull of a ship, and using strip line copper foil, for example. The examples are merely illustrative.

In view of the above, it will be seen that the several objects and advantages of the present invention have been achieved and other advantageous results have been obtained.

Having thus described the invention, what is claimed and desired to be secured by Letters Patent is:

1. A method of killing prokaryotic accretions comprising:
   providing a transmission appliance adapted to emit radio frequency energy to a conductor;

applying said transmission appliance to said conductor;

transmitting a frequency of at least about seven GigaHertz (GHz);

providing an electrode remote from said transmission appliance on said conductor, and producing a standing wave on said conductor at a frequency effective to kill prokaryotes in said prokaryotic accretion.

2. The method of claim 1 wherein said electrode is a grounded dispersive electrode.

3. The method of claim 1 wherein said radio frequency energy has a wavelength of between seven and twelve GigaHertz.

4. The method of claim 1 wherein said conductor is within an animal, said conductor being subcutaneous.

5. The method of claim 4 wherein said animal is a mammal.

6. The method of claim 5 wherein said mammal is a human.

7. The method of claim 5 wherein said conductor is an implanted, metallic conductor.

8. The method of claim 1 wherein said frequency is transmitted for a maximum of about five seconds.

9. The method of claim 1 wherein said frequency is transmitted at a power of about at least one hundred milliwatts (100 mW).

10. An apparatus for sterilizing a conductor comprising:

a source of radio frequency energy;

a conductor;

a transmission wire for connecting the source of radio frequency to the conductor; and an electrode spaced an effective distance from said transmission wire to produce a standing wave.

* * * * *